(12) United States Patent
Allington et al.

(10) Patent No.: US 6,997,683 B2
(45) Date of Patent: Feb. 14, 2006

(54) HIGH PRESSURE RECIPROCATING PUMP AND CONTROL OF THE SAME

(75) Inventors: Robert W. Allington, Lincoln, NE (US); Scott L. Blakley, Omaha, NE (US); Henry L. Walters, Lincoln, NE (US)

(73) Assignee: Teledyne Isco, Inc., Lincoln, NE (US)

( * ) Notice: Subject to any disclaimer, the term of this patent is extended or adjusted under 35 U.S.C. 154(b) by 37 days.

(21) Appl. No.: 10/340,817

(22) Filed: Jan. 10, 2003

(65) Prior Publication Data

US 2004/0136833 A1    Jul. 15, 2004

(51) Int. Cl.
*F04B 49/20* (2006.01)

(52) U.S. Cl. .................... 417/18; 417/22; 417/44.1

(58) Field of Classification Search .............. 417/44.1, 417/18, 20, 22; 418/40; 210/101, 138, 198.2
See application file for complete search history.

(56) References Cited

U.S. PATENT DOCUMENTS

| | | | |
|---|---|---|---|
| 3,563,672 A | 2/1971 | Bergstrom | 417/45 |
| 3,597,114 A | 8/1971 | Hrdina | 417/265 |
| 3,787,882 A | 1/1974 | Fillmore | 346/75 |
| 3,847,507 A | 11/1974 | Sakiyama | 417/22 |
| 3,855,129 A | 12/1974 | Abrahams | 210/198 C |
| 3,917,531 A * | 11/1975 | Magnussen | 210/101 |
| 4,045,343 A | 8/1977 | Achener et al. | 210/101 |
| 4,108,574 A | 8/1978 | Bartley et al. | 417/19 |
| 4,128,476 A | 12/1978 | Rock | 210/31 C |
| 4,131,393 A | 12/1978 | Magnussen | 417/22 |
| 4,137,011 A | 1/1979 | Rock | 417/22 |
| 4,155,683 A | 5/1979 | Mochizuki | 417/269 |
| 4,180,375 A | 12/1979 | Magnussen | 417/22 |
| 4,225,290 A | 9/1980 | Allington | 417/18 |
| 4,233,156 A * | 11/1980 | Tsukada et al. | 210/101 |
| 4,260,342 A * | 4/1981 | Leka et al. | 417/458 |
| 4,326,837 A | 4/1982 | Gilson | 417/12 |
| 4,352,636 A * | 10/1982 | Patterson et al. | 417/22 |
| 4,359,312 A | 11/1982 | Funke | 417/18 |
| 4,420,393 A | 12/1983 | Smith | 210/101 |
| RE31,586 E | 5/1984 | Magnussen | 417/22 |
| 4,448,692 A | 5/1984 | Nakamoto | 210/656 |
| RE31,608 E | 6/1984 | Magnussen | 417/22 |
| 4,600,365 A | 7/1986 | Riggenmann | 417/246 |

(Continued)

OTHER PUBLICATIONS

William J. Palm III, "Control Systems Engineering", 1986, John Wiley & Sons, Inc., pp. 19-21.*

(Continued)

*Primary Examiner*—Charles G. Freay
(74) *Attorney, Agent, or Firm*—Sturm & Fix LLP

(57) ABSTRACT

Pumping for chromatograph applications calls for constant flow at high pressures and for accurate control of liquid composition. A two-cylinder pump, and associated controls provide an accurate, fixed flow rate. During the initial portion of the pumping stroke of a first piston, while its check valve remains closed, a second piston provides all the flow required at a fixed rotational speed. Once the pressure inside the first piston's cylinder has reached that of the discharge and its discharge check valve opens, the control system switches to a constant-pressure control mode, to maintain a fixed flow rate. Constant-pressure control is switched off when the second piston's discharge check valve closes, and pump control returns to fixed rotational speed. Determining the angular displacement at which to effect these control-mode switches is carried out by monitoring changes in the discharge pressure.

42 Claims, 10 Drawing Sheets

U.S. PATENT DOCUMENTS

| | | | | |
|---|---|---|---|---|
| 4,767,279 A | * | 8/1988 | Dourdeville et al. | 417/18 |
| 4,820,129 A | * | 4/1989 | Magnussen, Jr. | 417/18 |
| 4,913,624 A | * | 4/1990 | Seki et al. | 417/2 |
| 4,919,595 A | | 4/1990 | Likuski | 417/18 |
| 4,981,597 A | | 1/1991 | Allington | 210/656 |
| 5,286,177 A | | 2/1994 | Johann | 417/415 |
| 5,755,559 A | | 5/1998 | Allington | 417/53 |

OTHER PUBLICATIONS 8 pages—entitled MODEL 100 Solvent Metering System Operators Manual—Manufactured by ALTEX Scientific Inc.

4 pages—entitled ALTEX High Performance Liquiud Chromatography—showing Models 100A and 101A HPLC Solvent Metering Systems.

7 sheets—entitled ALTEX Model 100—HPLC Solvent Metering System—A New Standard for High-Speed Liquid Chromatography.

4 sheets—entitled Altex Chromatogram—by Altex Scientific Inc.

2 sheets—by Knauer—(in German).

2 sheets—by Knauer—entitled Pulse-free High Pressure Pump System for Liquid Chromatography.

* cited by examiner

HIGH PRESSURE RECIPROCATING PUMP AND CONTROL OF THE SAME

BACKGROUND OF THE INVENTION

1. Field of the Invention

The present invention relates generally to a method and apparatus for configuring and controlling a two-cylinder, reciprocating pump such that it pumps a constant volumetric flow rate at any discharge pressure. Such a pump is useful for applications such as chromatography, which requires accurate, constant flow rates from pumps at high and variable discharge pressure. More particularly the present invention utilizes a constant rotational speed for most of a given cycle, but utilizes pressure control (and slightly varying rotational speed) for a portion of the cycle in which the flow would normally increase if rotational speed is maintained a constant. As a consequence, the pressure control acts to control the rotational speed to an amount very close to the previous speed. Another advantage is a largely constant volumetric input flow rate which improves accuracy of low pressure gradient forming. A logic system is incorporated to provide accurate low pressure gradient former switching, corrected for the depressurization of each of the pump cylinders before their refill.

2. Background Art

Pumps used for liquid chromatography have stringent requirements to deliver constant and accurate flow rates over a range of discharge pressures. Reciprocating (or piston) pumps are usually employed for this purpose for reasons including their relatively fixed displacement.

Present-day piston pumps for chromatography are often two-cylinder pumps where the pistons are actuated by cams—usually one cam per piston. The cam profiles are designed so that the sum of the positive (pumping) speeds of the pistons is a constant if the rotational speed is constant. As one piston decelerates near the end of its delivery stroke, the other cylinder has finished filling and the piston accelerates as it begins its stroke toward the cylinder head. The result of the constant sum of piston velocities in this interval is, if both discharge check valves are open, the total flow rate is constant.

When the pump discharge pressure is low (less than about 10 atmospheres, absolute), the flow rate remains constant with constant rotational speed. Liquids are, in fact, not truly incompressible. A measure of a fluid's "compressibility" is the bulk modulus of elasticity, $E_v$, defined as $$E_v = -V \frac{dp}{dV}$$

where p is pressure and $V$ is volume. The bulk modulus of elasticity is larger for a liquid than a gas, but is not infinite. According to the above equation, when pressure changes, so does the volume of a liquid. Because of this volume change, and because the components of the pump are non-rigid, the actual travel distance from bottom dead center until the discharge check valve opens becomes non-negligible. The result is, during this portion of the cycle, fluid is being pumped from a single cylinder only, while the shape of the cam profile is increasing or keeping a piston's speed constant.

Thus, at a constant rotational speed, the flow rate is less than the constant value required. Early pumps used an accumulator to smooth the pressure and flow rate in time. In present-day pumps, the instantaneous flow deficiency is made up by increasing the rotational speed of the pump by the control system in this region.

To maintain a constant flow rate, the pump discharge pressure should remain constant. Present-day pumps use either a flow measurement or pressure measurement as a process variable within a high-speed control system to maintain constant flow rate. The manipulated variable is the pump's rotational speed. So, during the period in which a piston is traveling toward its head while its discharge check valve is closed, the pump rotational speed must increase.

Control of the speed of the pump is based on pump discharge pressure most of the time, despite the fact that constant speed is required through the majority of the pump's cycle. Control based on pressure is subject to the noise and response time of the sensor. In addition, the flow rate into the pump during the inflow parts of the pump cycle is not well controlled, making it difficult to produce accurate chromatography eluant composition gradients by repetitively and synchronously switching eluant compositions at the pump inlet. This is referenced in the art as "low pressure gradient forming" and has the advantage that it requires only a single high-pressure pump, rather than the usual dual pump.

There is, therefore, a need for a pump to accurately deliver a constant flow rate fluid of controlled (gradient) composition regardless of the discharge pressure.

SUMMARY OF THE INVENTION

A purpose of this invention is to provide a method and device capable of producing constant flow rates at a high discharge pressure. It has particular application to chromatography. To accomplish this purpose, a two-cylinder pump is used, each piston being driven by a separate cam. Both cylinders provide constant flow at high pressure, but are placed less than the usual 180° apart over most of the rotation. For the preferred embodiment, the delivery stroke of each piston is 240° and the refill stroke is 120°. The maximum of a refill stroke of one piston leads the maximum of the delivery stroke of the other piston, and conversely so, by 60°. However, the fluid delivery strokes are 180° apart.

The pumped fluid has a finite bulk modulus of elasticity and the components of the pump are incompletely rigid. Therefore, during a portion of the cycle of each piston, the piston is traveling toward its head, but no fluid is being delivered. This is because the pressure inside the cylinder has not yet reached the value of the pressure in the discharge of the pump, so the discharge check valve is closed. This portion of the cycle of the first piston is called recompression. During recompression for one piston, the cam profile for the other piston is shaped such that the other piston is able to deliver the required flow rate. When the pressure inside the cylinder of the first piston reaches the discharge pressure, the discharge check valve for the first piston opens. Because the second piston is still able to supply the full flow rate, if the rotational speed remains constant, the flow rate and discharge pressure will increase. To avoid this unwanted increase in flow rate, the pump's rotational speed must decrease.

Shortly thereafter, the second piston starts to withdraw (retract away from its head), decompressing the high-pressure liquid in the chamber. When this decompression portion of the cycle is complete, the second piston's inlet check valve opens and inlets liquid of programmed concentration or composition from a source at (approximately) atmospheric pressure.

Because of the varying flow rate at constant rotational speed, a control system manipulating rotational speed is incorporated into the pump system. During the majority of the pump's cycle, a constant rotational speed will result in a constant flow rate. It is only during the brief period, already described, when the first discharge check valve has just opened, and before a second discharge check valve closes, that the rotational speed must be altered. Therefore, during most of the pump's cycle, the rotational speed is fixed. When the first piston's discharge check valve opens, the control system switches to pressure control to decrease the rotational speed, appropriately. Discharge pressure control remains in effect until the discharge check valve of the second piston closes, at which time the pump is returned to fixed speed control.

To effect the required speed decrease, a high-speed control system monitors the pump discharge pressure. This discharge pressure is measured during the portions of the cycle in which the rotational speed is fixed and this pressure is used as a set point for the pressure control system. During the portion of the cycle in which the pressure control system is manipulating the rotational speed, the pressure will be controlled to the pressure set point.

To determine what portion of the cycle in which to apply pressure control, the pressure and the angular position of the cam and motor shaft are monitored continuously. The opening of a discharge check valve during fixed-speed operation indicates the completion of recompression and can be sensed by a pressure increase. This sudden increase in pressure is correlated to the angular position of the pump shaft, and this opening angular-related volume displacement is stored in memory. One such opening volume displacement is stored for each of the two cylinders, comprising a first storage mode. In the same manner, when a discharge check valve closes, due to a piston having come near the end of its stroke, the discharge pressure will experience a decrease as the cam crosses over top high center. This decrease in pressure is correlated to the angular position of the camshaft, and this closing angular position may be stored in memory. The pressure disturbances are detected through a high gain factor and are not usually noticeable at the high pressure liquid outlet. One such set of opening and closing angular values are stored for each of the two cylinders. A second sensing uses a cam or photocell detector to sense when a piston goes over bottom dead center (fully retracted).

Since each of the recompression and decompression liquid cycles are very nearly thermodynamically reversible, the decompression volume is very nearly equal to the recompression volume. As indicated above, the two respective recompression volumes are stored in memory. These stored amounts are used respectively as decompression points to detect the end of decompression of a respective cylinder. This is necessary for accurate synchronization of an incorporated low pressure gradient former. By continuing to monitor the pressure, anticipatory, automatic adjustments to these stored displacements are made during operation. An unusual cam design provides for constant fluid inlet velocity as well as constant fluid outlet velocity with respect to constant speed of the camshaft. Constant inlet velocity is not strictly necessary but it decreases the cost and increases the reliability of providing high gradient accuracy.

BEST MODE FOR CARRYING OUT THE INVENTION

Figure 1:
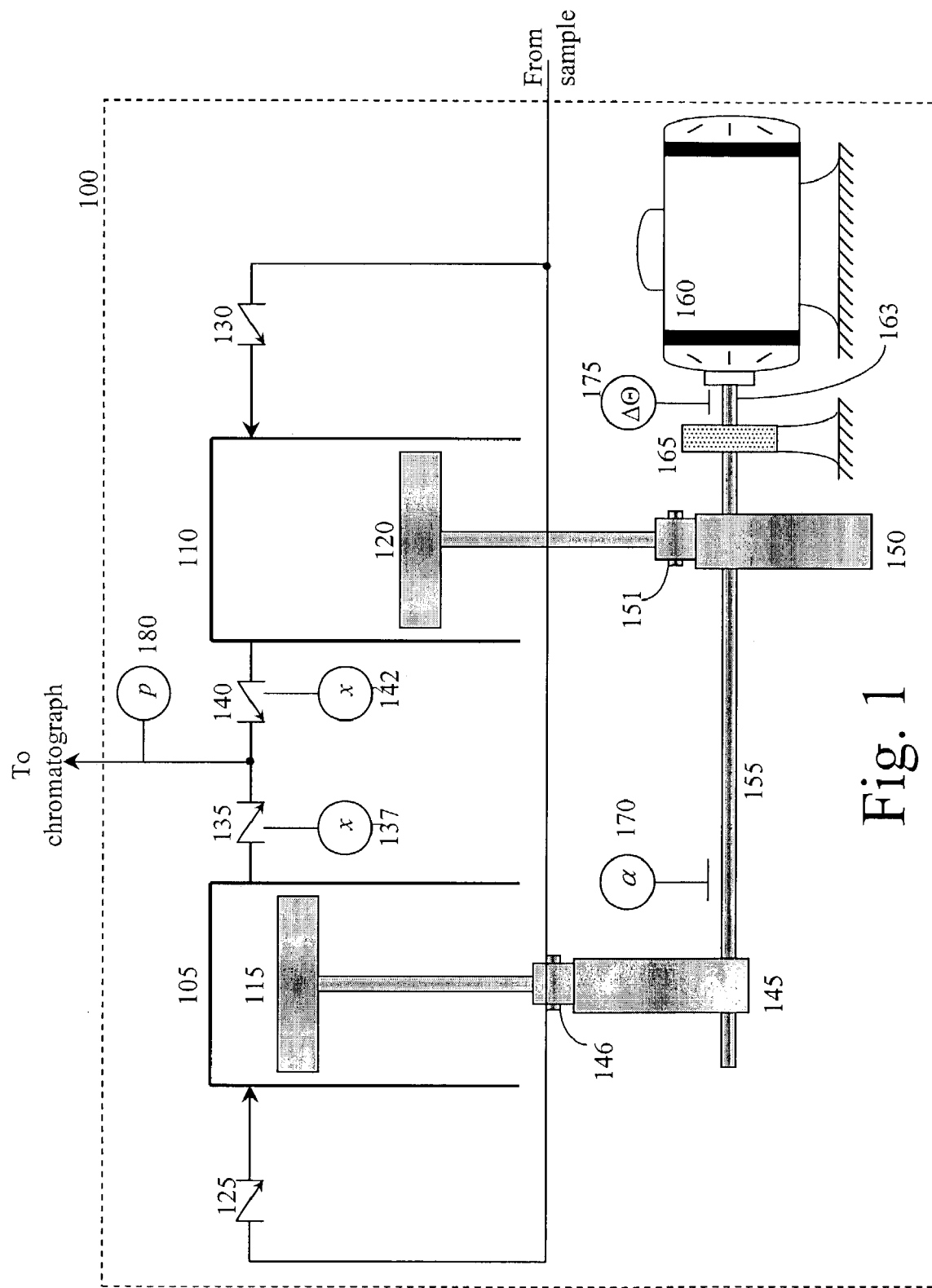
FIG. 1 shows a schematic of a pump.

A schematic depiction of a two-cylinder pump 100 is shown in FIG. 1. Inside the two cylinders 105 and 110, pistons 115 and 120 oscillate. The flow entering from the sample passes through inlet check valves 125 and 130 that permit the fluid to pass into the cylinder through the inlet line, but disallow the fluid from exiting through the inlet line. Discharge check valves 135 and 140 function to permit the flow of fluid from the pump cylinders 105 and 110 but to disallow the fluid from reentering the cylinder from the discharge line.

The velocities of the pistons 115 and 120 are dictated by cams 145 and 150 that are both driven by a single shaft 155 and followers 146 and 151. A variable speed electric motor 160 provides the motive power to the slower-rotating camshaft 155 through gear box 165.

Several transmitters are shown in FIG. 1. The angular position transmitter 170 provides a value for the angular displacement, $\alpha$, of the camshaft 155. The angular increment transmitter 175 provides a value of the motor shaft's 163 incremental angular position $\Delta\theta$. Shaft speed $\omega$ is equal to the first temporal derivative of $\theta$, or the update rate of $\Delta\theta$ that takes place in rate converter 287. The pump discharge pressure transmitter 180 provides a value for the pump discharge pressure, p, downstream of the discharge check valves 135 and 140. These three values are used by the control system to a maintain constant flow rate. Two other transmitters 137 and 142 are optional. They are used to detect the opening of check valves 135 and 140, respectively.

Figure 2:
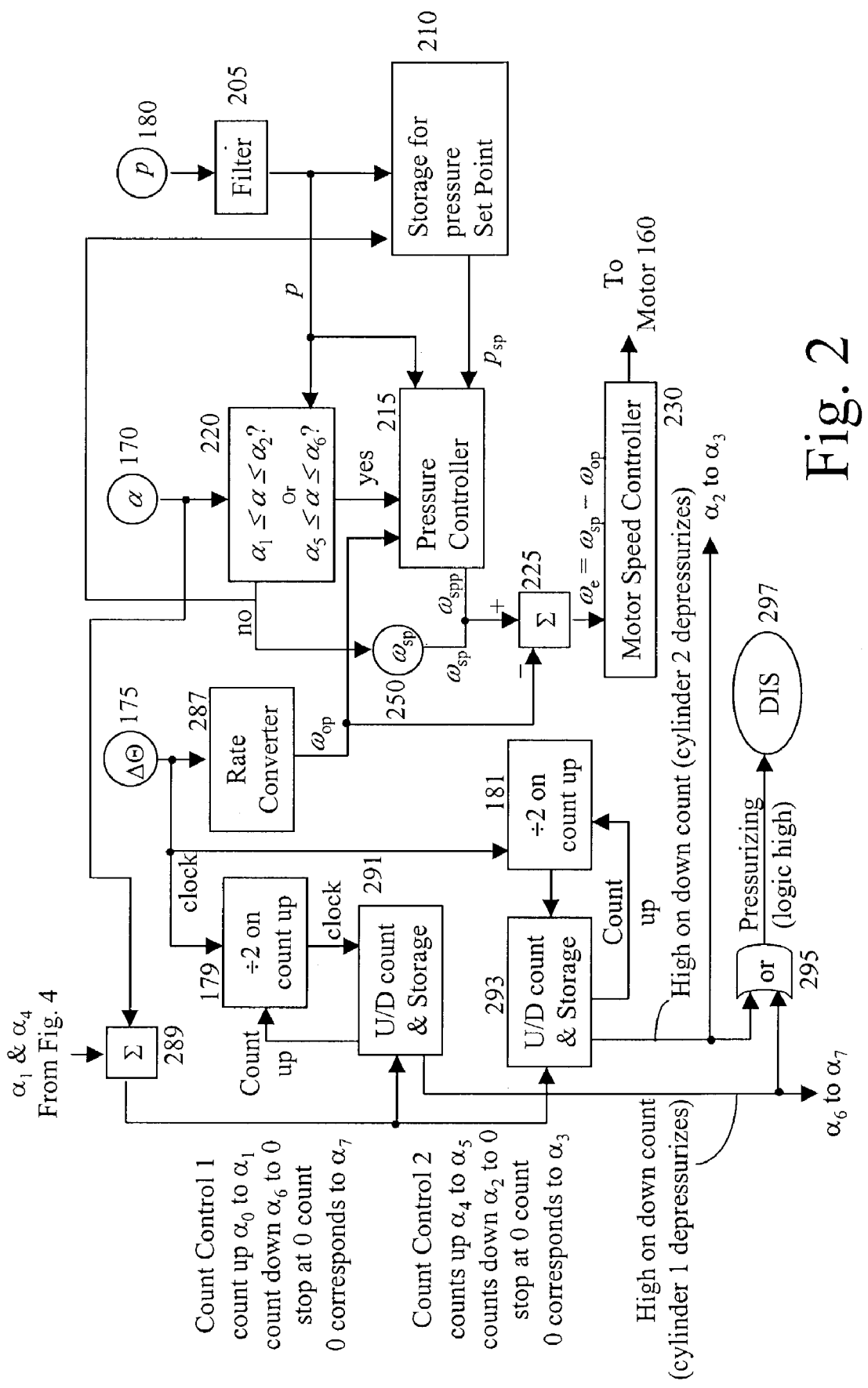
FIG. 2 shows a control scheme.

A schematic of a representative control system is shown in FIG. 2. FIG. 2 shows the controller using random logic to clarify operation. A similarly functional microprocessor could be substituted.

Figure 3:
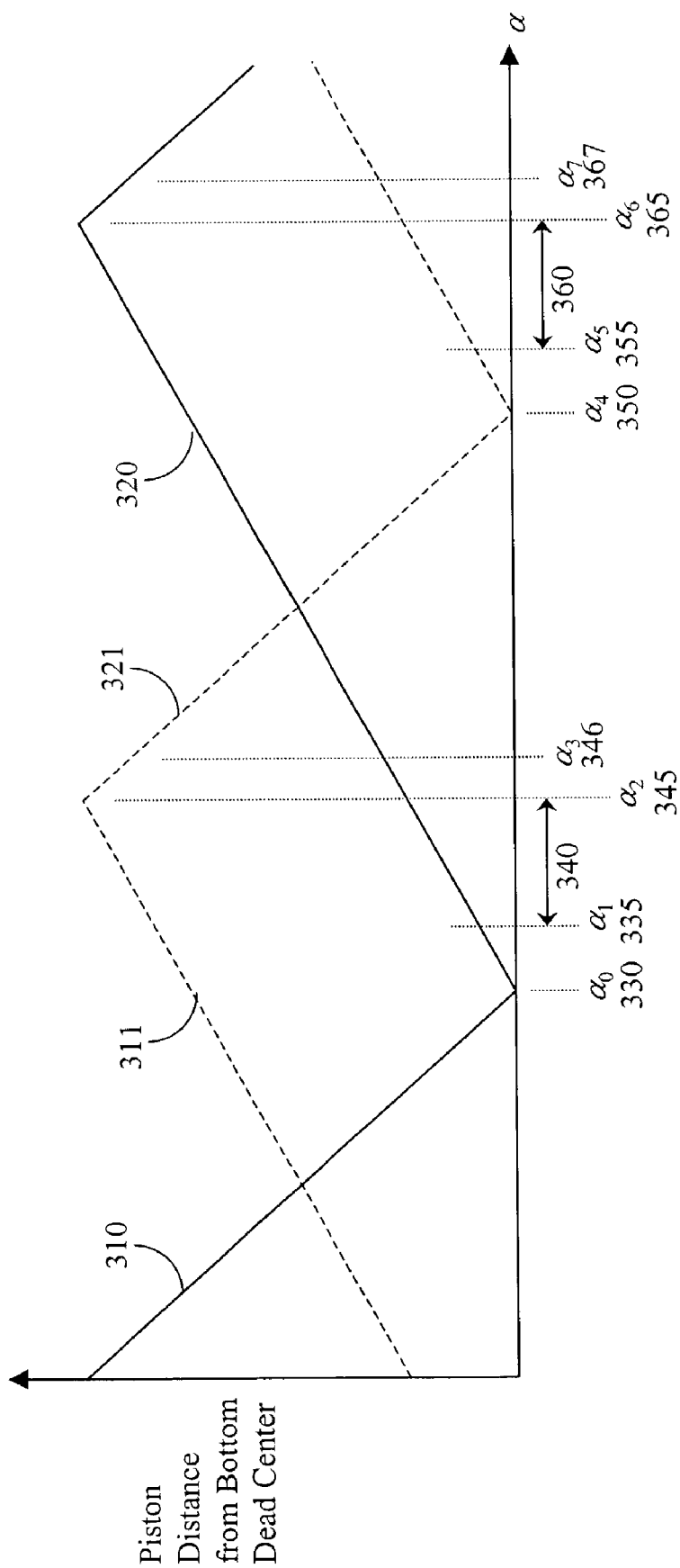
FIG. 3 shows a plot of piston displacement versus angular displacement.

The transmitters 170, 175, and 180 measuring values of angular displacement, $\alpha$, incremental angular position, $\Delta\theta$, and pump discharge pressure, p, respectively, are shown once again. The pressure signal is filtered, if necessary, in filter block 205. The filtered pressure value is then passed on to storage block 210. Storage block 210 accepts one or more readings outside the regions $\alpha_1 \leq \alpha \leq \alpha_2$ 340 and $\alpha_5 \leq \alpha \leq \alpha_6$ 360 (as shown in FIG. 3 and explained below). If more than one reading is taken, the values may be averaged to smooth out variations due to noise, etc. The resulting value is used as the discharge pressure set point, $p_{sp}$. The discharge pressure set point proceeds to pressure controller 215 where it is actively used inside the regions $\alpha_1 \leq \alpha \leq \alpha_2$ 340 and $\alpha_5 \leq \alpha \leq \alpha_6$ 360 (FIG. 3) as the pressure controller's 215 set point.

The value of the filtered pressure is also received by pressure controller 215 as its process variable. The error between the process variable, p, and the set point, $p_{sp}$ is calculated by the controller and a rotational speed set point, $\omega_{sp}$, calculated using a control algorithm such as a Proportional Integral Derivative (PID) algorithm. The value of the rotational speed set point as calculated by the pressure controller is only used by the motor speed controller 230 (via the error block 225) if $\alpha_1 \leq \alpha \leq \alpha_2$ or $\alpha_5 \leq \alpha \leq \alpha_6$ as determined by the logic block 220. The rate converter 287 converts $\Delta\theta$ composition pulses from sensor 175 on the motor shaft 163 to a signal representing the operating speed $\omega_{op}$. Block 225 allows the manual entry of the set point speed $\omega_{sp}$ 250.

If logic block 220 determines that the angular displacement, $\alpha$, is outside the closed regions [$\alpha_1$, $\alpha_2$] and [$\alpha_5$, $\alpha_6$], an angular speed set point, $\omega_{sp}$, 250 is pass the error block 225, which subtracts the actual operating speed $\omega_{op}$ from $\omega_{sp}$ 250. The result of error block 225 is a speed error signal $\omega_e$. The speed error signal is sent to the motor speed controller 230 as shown. The motor speed controller 230 uses the error value of the angular speed, $\omega_e$ for maintaining the motor speed, $\omega_{op}$, at the desired value.

A simplified depiction of the pistons' distances from their respective bottom dead centers is shown in FIG. 3. Note that the fluid delivery times are twice the refill times. The duration of line 310 corresponding to inletting to the first cylinder is one half that of the line 320 corresponding to the discharge of this cylinder. The same applies to line 321 and 311 for the other cylinder.

We will focus just on the piston for which the solid line is plotted in FIG. 3.

Fluid is being drawn into the cylinder through most of the piston's travel away from the cylinder head. This portion of travel is shown as the straight line 310. Through most of the piston's travel toward its cylinder head, fluid is being expelled to a load such as a chromatograph. This portion of travel is the straight line labeled 320. At $\alpha_0$ 330, the piston is at bottom dead center. Its velocity is momentarily zero. Both its inlet and discharge check valves are closed. The piston begins its course away from bottom dead center toward $\alpha_1$ 335. The process taking place when the camshaft is between the angular positions, $\alpha_0$ 330 and $\alpha_1$ 335, is called "recompression:" during this portion of the stroke, the pressure in the cylinder increases from the suction pressure to the outlet pressure. At $\alpha_1$ 335, recompression is completed within the corresponding cylinder and the discharge check valve 135 opens. Also at $\alpha_1$ 335, the motor speed controller's 230 set point switches from a fixed value, $\omega_{sp}$, emanating from set point block 250 to a variable value, $\omega_{spp}$, calculated by the constant pressure controller 215. At this time, both cylinders are delivering liquid. This mode of control (utilizing a different—approximately $\omega_{op}$/2—rotational speed set point, $\omega_{spp}$, from the constant pressure controller 215) continues through the region 340 between $\alpha_1$ 335 and $\alpha_2$ 345. Once past $\alpha_2$ 345, the angular speed set point sent to the error block 225 reverts back to a fixed value 250, $\omega_{sp}$.

The same cycle is experienced by the other piston, having the plot of its distance from bottom dead center versus its angular displacement depicted by the dashed line in FIG. 3. The region in which the rotational speed set point, $\omega_{spp}$, emanates from pressure controller 215 is the interval 360 between $\alpha_5$ 355 and $\alpha_6$ 365.

Figure 4:
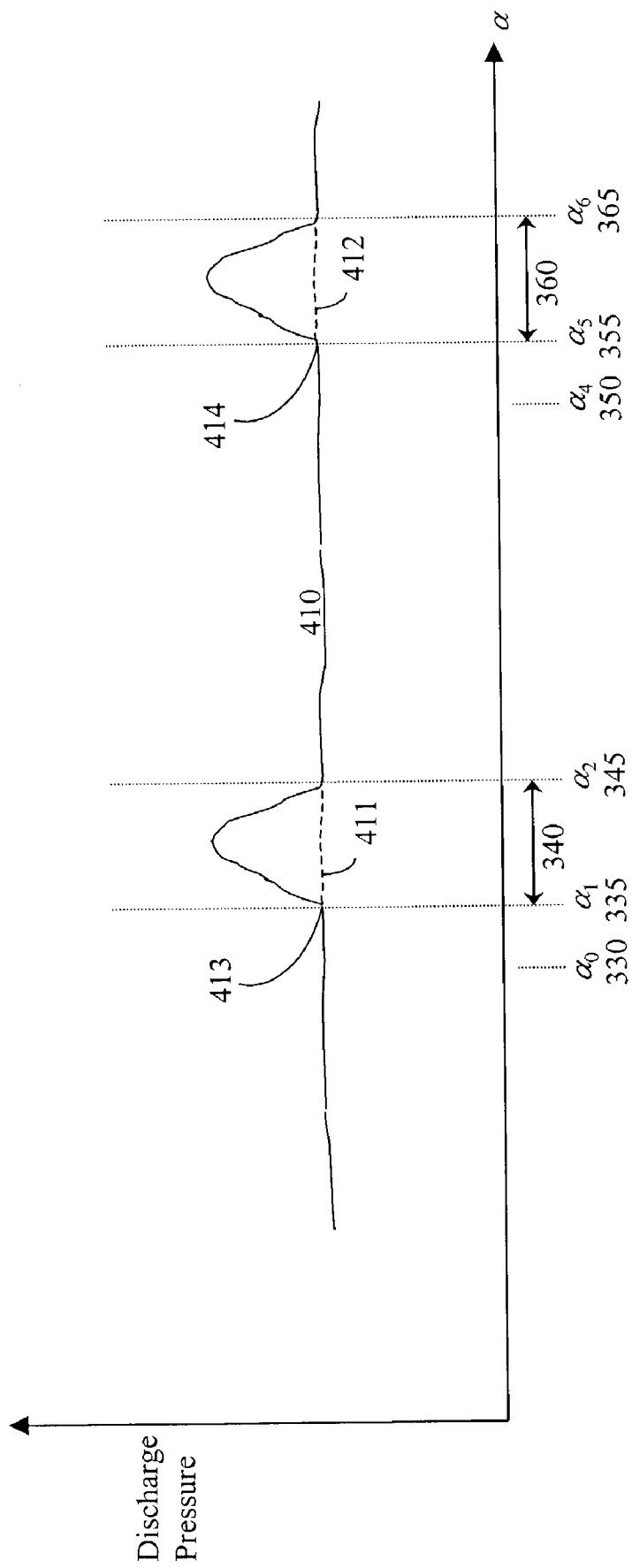
FIG. 4 shows a plot of pressure versus angular displacement.

To determine the angular displacement values $\alpha_1$ 335 and $\alpha_2$ 345 (and $\alpha_5$ 355 and $\alpha_6$ 365) at which to start and stop constant pressure control, the pressure signal is analyzed in a high-speed data analyzer that checks for a sudden change in the pressure signal 410 shown in FIG. 4. Without the constant pressure controller 215 of this invention, the pressure would rise as shown at 413 or 414 when both pump heads are delivering fluid. With the pressure controller 215, during the pressure controlled regions 340 and 360 of the cycle, the motor slows down to keep the pressure substantially constant is shown by the dashed lines 411 and 412.

Valid values of $\alpha_1$ 335 and $\alpha_2$ 345 (and $\alpha_5$ 355 and $\alpha_6$ 365) can be determined, for instance, by calculating the first derivative of the signal with respect to time, or by calculating the frequency content of the signal and detecting when the amplitudes of higher frequency values change sharply.

Another aspect of this invention is associated with the induction of solvent into the pump. To permit a selection of solvents to be accurately mixed in the pump 100, a solenoid valve tree assembly 560, shown in FIG. 5, resides between the solvent source 544 and the pump 100. The use of a valve tree, in which at most one of several paths can possibly be open at a time to a plurality of solvent sources 544, simplifies switching functions, as it allows abundant time for the valves to mechanically return after deactivation. When a flow path through the vale tree assembly 560 between solvent source 544 and pump 100 is "open," fluid will not flow if the pump's inlet check valves are closed. Solvents are delivered to pump 100 during the inlet strokes 310 and 321 of the pistons 115 and 120. The valve tree assembly 560 includes two three-port valves, which are a first electrically actuated valve 540 and a second electrically actuated valve 550. The solvent source 544 includes three solvent sources 510, 520 and 530. If neither valve is actuated, the solvent will flow from solvent source A 510, through valves 540 and 550 to pump 100. When valve 550 is actuated, its port to valve 540 is closed while its port to solvent source C 530 is open. Only solvent C 530 will flow in this condition. Any time it is required that either solvent A or solvent B 510 be flowing into pump 100, valve 550 must be deactuated. When valve 540 is deactuated, its port to solvent A 510 is open. In order for solvent B 520 to flow into pump 100, valve 540 must be actuated while valve 550 must be deactuated. In this way, any of the three solvents may be drawn into pump 100 while all other solvents are disallowed from flowing.

In practice, actuation of each of the valves 540 and 550 is carefully timed within actuation logic controller 570 during the intake strokes 310 of the pump's cycle such that each of the three solvents 510, 520, and 530 are accurately metered into pump 100. This is accomplished by a number of complementary means. First is measuring the time delay of each valve's opening, which happens at an only roughly fixed time after the valve is electrically activated. This delay time is electronically stored and used to correct the activation delay time of the same valve in the following mixing cycle. This is described more fully in U.S. Pat. No. 5,158,675 assigned to Isco, Inc. and incorporated herein by reference.

Figure 8:
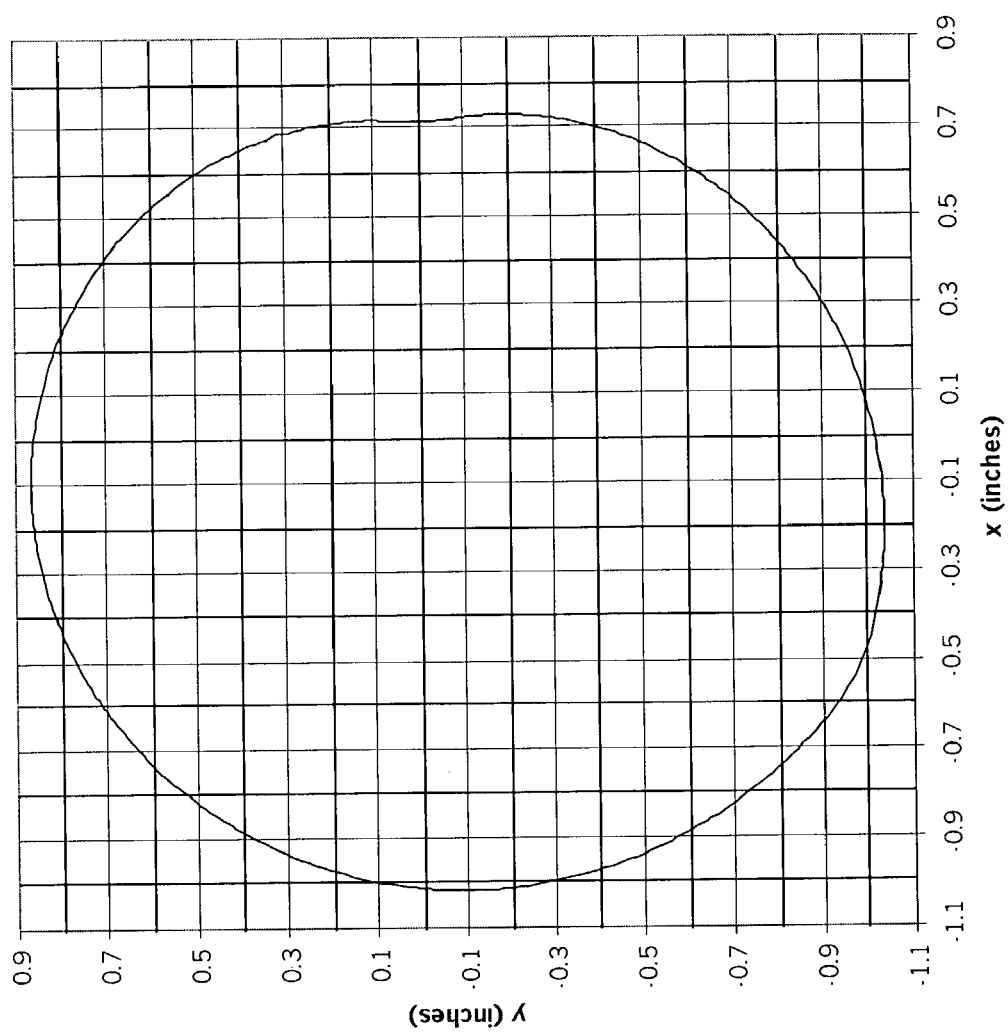
FIG. 8 shows the cam.
Figure 9:
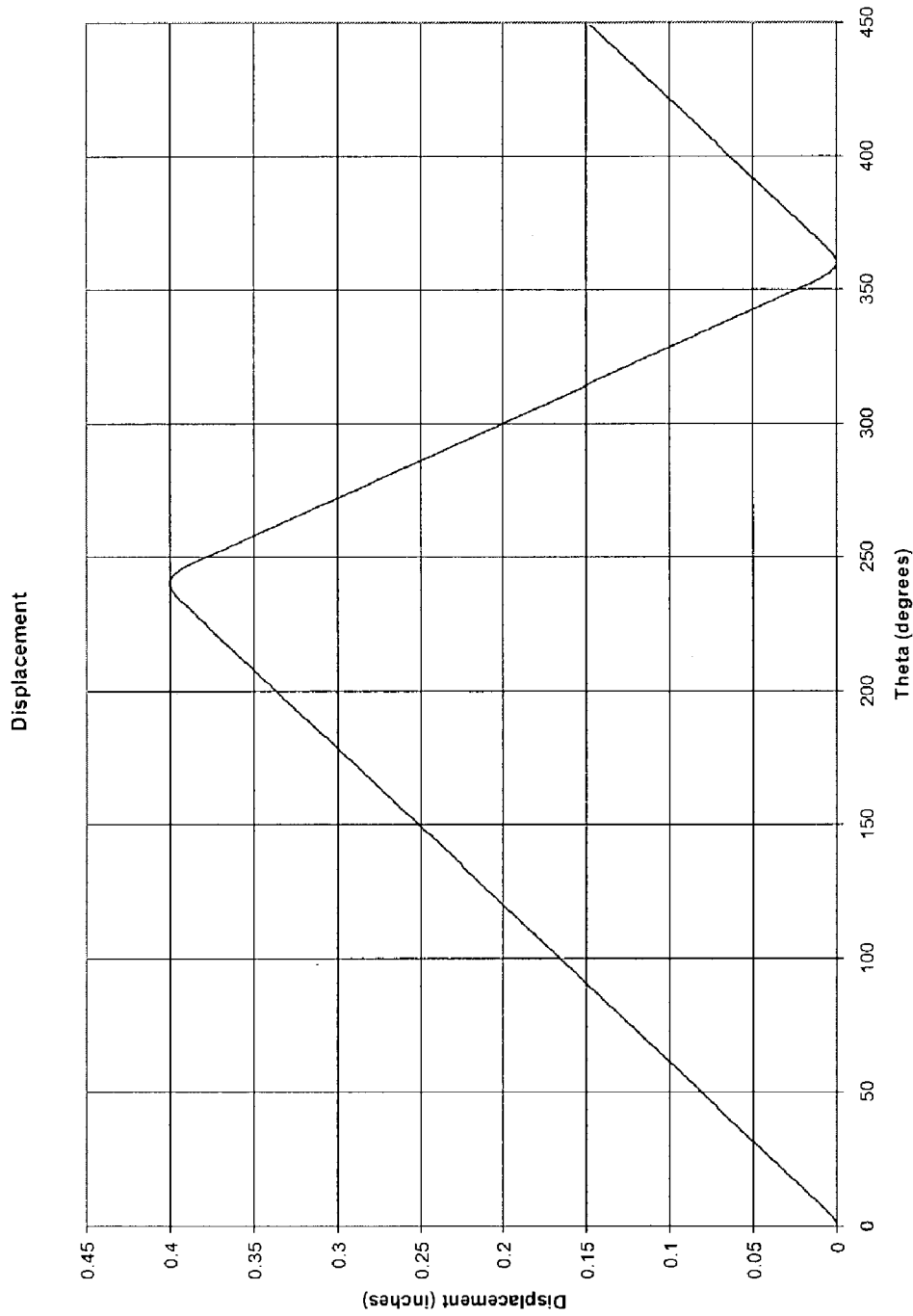
FIG. 9 shows the displacement profile of the cam with cam follower.
Figure 10:
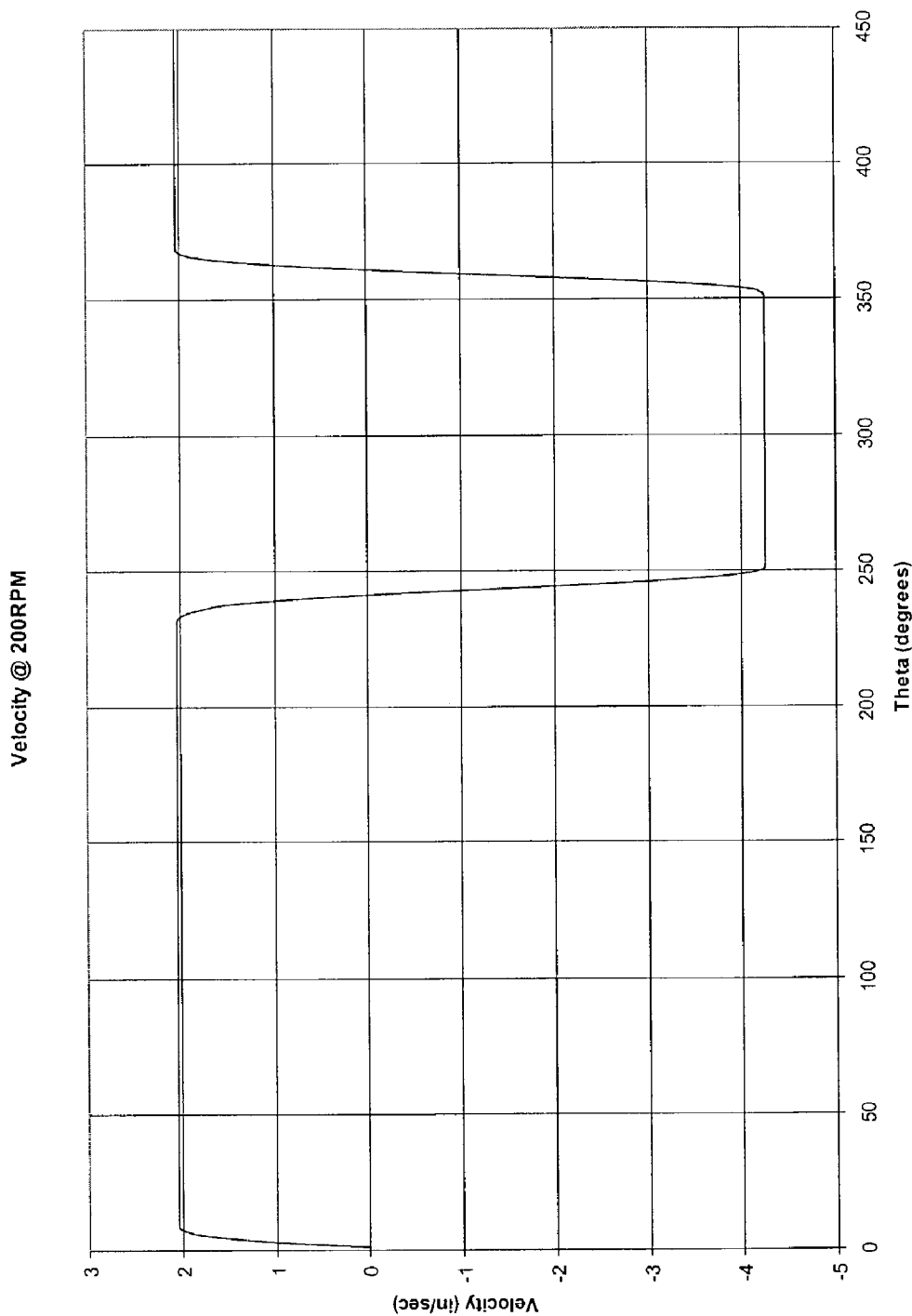
FIG. 10 shows the velocity profile of the cam with cam follower.

Another aspect of this invention is that the inlet stroke of each pump occurs at a time during a period of constant displacement rate and constant rotational speed of the associated cam 145 or 150. These displacements are those for using needle bearing style, ⅞ inch diameter roller cam followers 146 and 151 riding respectively on the cams 145 and 150 (FIG. 1). The cams 145 and 150, a profile of which is shown in FIG. 8, are designed such that the displacement rates are linear using these cam followers. The actual displacement versus angular position is shown in FIG. 9. The piston velocity is, therefore, remarkably constant as can be seen in FIG. 10. FIG. 3 shows cam and follower displacements that come to pointed peaks for clarity. It is more practical to use rounded peak segments in actual mechanical systems. This does not affect the accuracy of operation since it is based on reading and comparing pressure and cam profiles on an on-line cam angle to piston (or cam) displacement in such a way that error due to fuzzy or rounded flow rate peaks is cancelled. This cam arrangement combined with the operation circuit shown in FIG. 2 greatly simplifies and increases the accuracy of the gradient valve switching.

Figure 5:
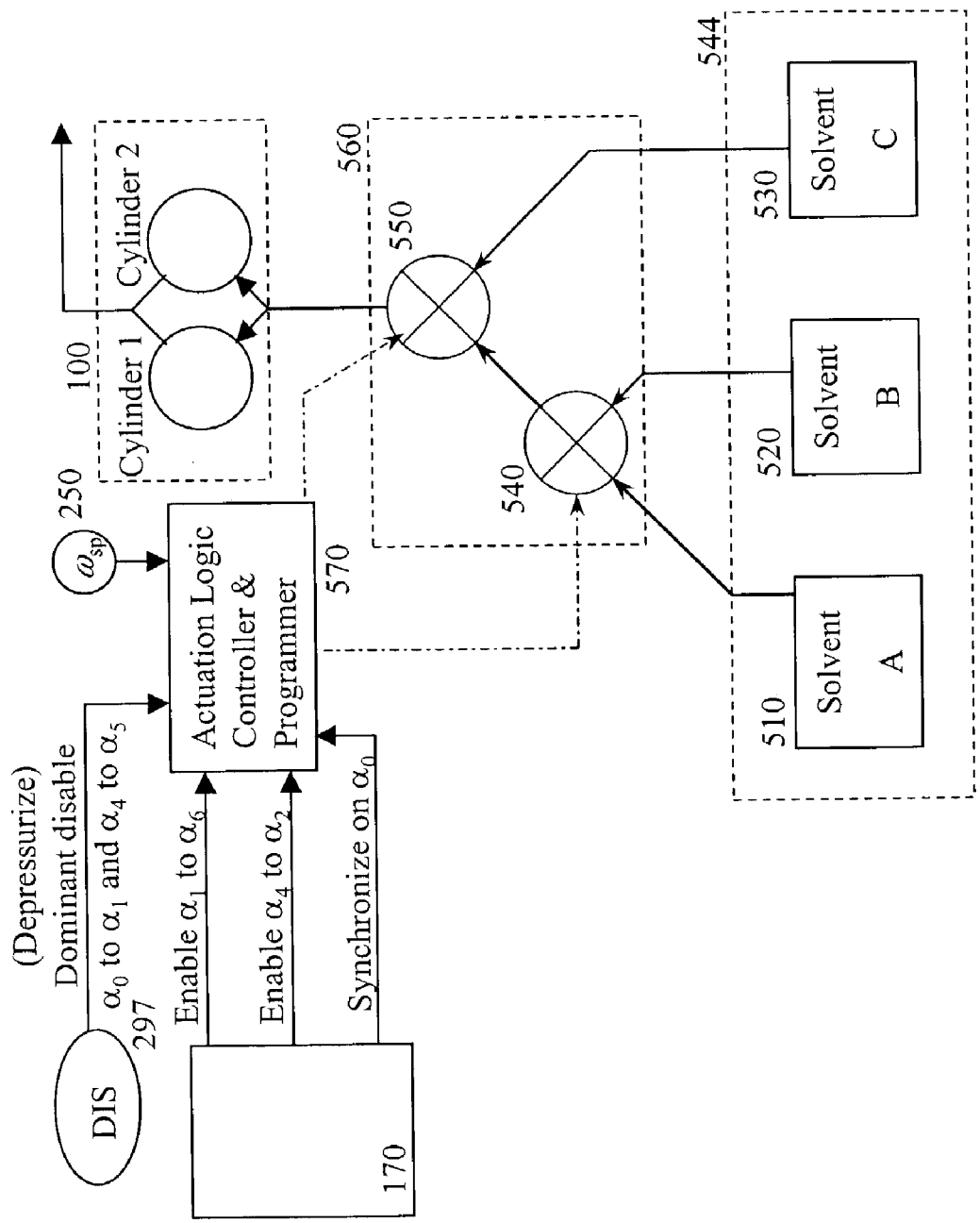
FIG. 5 shows a pump inlet assembly, including solvent sources, valve tree, and actuation logic controller.

Calculating of completion of decompression, the time a pump cylinder starts filling, is necessary for starting the gradient former, if accurate gradients are to be made (FIG. 2). Decompression is shown as the region between $\alpha_2$ 345 and $\alpha_3$ 346 in FIG. 3 for one piston. The other piston's decompression region lies between $\alpha_6$ 365 and $\alpha_7$ 367. $\Delta\theta$ is the incremental camshaft position and is detected by $\Delta\theta$ photocell interrupter 175. The rate at which $\Delta\theta$ changes is proportional to $\omega_{op}$, the motor shaft rotational speed operating point. The rate converter 287 converts $\Delta\theta$ to $\omega_{op}$ and transmits it to the speed error calculation block 225 and pressure controller 215. $\Delta\theta$ is also counted by the two-gated counters 291 and 293, which prevent gradient and gradient cycles from operating during depressurization. During recompression, the gated counter 291 counts up from $\alpha_0$ 330 (cam determined) to $\alpha_1$ 335 (pressure determined) to determine repressurization of cylinder 1. The up count is first divided by two in the counter 179 because the delivery stroke is twice as long as the filling stroke. The signal processing may be compensated if necessary to match the cam peak profile, or the converse. Then the gated counter 291 down-counts the number of $\Delta\theta$ increments during the depressurization time of cylinder 1 from $\alpha_6$ 365 to $\alpha_7$ 367 the latter of which is a count down to zero, whereupon the counter stops. Angular position, $\alpha_0$ 330, is determined from the position of the camshaft 155. Angular position, $\alpha_1$ 335, is determined by a pressure increase 413. The difference between $\alpha_0$ 330 and $\alpha_1$ 335 equals twice the up-count angle from $\alpha_6$ 365 to $\alpha_7$ 367, the decompression angle for cylinder 1. ($\alpha_7$ 367 can be calculated since $\alpha_6$ 365 is determined by the cam and the difference, $\alpha_7-\alpha_6$, can be computed from the difference, $\alpha_0-\alpha_1$.) Cylinder 2 has its recompression/decompression angle computed similarly by gated counter 293. The gradient former shown in FIG. 5 is activated (refill) during operation from $\alpha_7$ to $\alpha_0$ for cylinder 1. The control for cylinder 2 is similar, activating the gradient former for $\alpha_3$ to $\alpha_4$.

Figure 7:
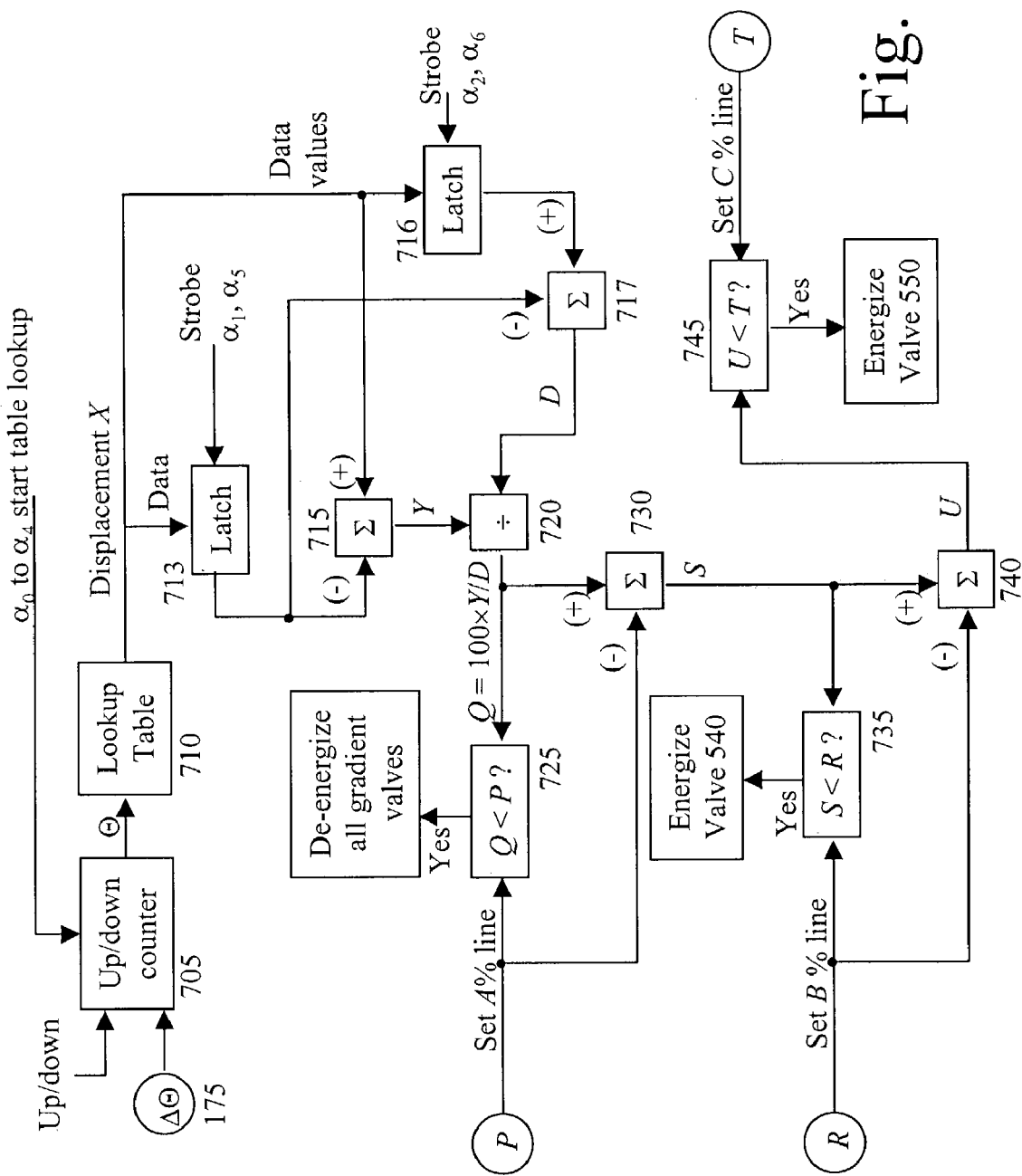
FIG. 7 shows a logic diagram for low pressure gradient forming.

Values of $\theta$ may be used for the program gradient operation, but corrected values proportional to actual displacement are better as they are not inaccurate because of small departures of cams from ideality. For example, it is not possible to make a robust cam that produces a point-change in slope as shown in FIG. 3 at $\alpha_2$. See FIG. 10 for comparison of results from a real cam. FIG. 7 shows the use of a lookup table (as seen in Appendix 1) to derive very accurate displacement values to enable accurate gradient forming.

Referring, now, to FIG. 7, the up/down counter 705 converts $\Delta\theta$ pulses from values from the angular increment sensor 175 to values of cam angle $\theta$. The lookup table 710 receives values of cam angle $\theta$ from the up/down counter 705 and outputs the corrected instantaneous cylinder displacement, X. However, this displacement is not corrected for the fact that flow does not begin when the piston is at bottom dead center (i.e. $\alpha_1$ 335 is greater than $\alpha_0$ 330). This correction may be done by subtracting the observed values of X at the angular value, $\alpha$, at which the discharge check valve opens and flow begins, that is, $\alpha_3$ 346 and $\alpha_7$ 367, calculated from $\alpha_1$ 335 and $\alpha_5$ 355 as inputted to Latch 713, which calculates the volume of recompression. By subtracting (in the summation block 715) the value of the displacement when the associated discharge check valve opens from the instantaneous cylinder displacement, the actual volume of fluid discharged from the cylinder, Y, is determined.

The total displacement, D, corrected for decompression is calculated in summation block 717 from knowledge of the total displacement determined from $\alpha_2$ and $\alpha_6$ 365, inputted to Latch 716; and the displacement associated with recompression.

These corrected volumes Y and D both have the proper zero base and spread. Dividing Y by D and multiplying by 100% in division block 720 produces a value equal to the instantaneous percentage of the volume, Q, delivered during a flow cycle.

The quotient, Q, is presented to a triple decision tree 725, 735, and 745 along with externally set and programmed gradient set point values for A %, B %, and C %. In the first decision block 725, the volume percent, Q, is compared directly with a set point, P, for the influx of solvent A. If the result of decision block 725 is true, all valves will be de-energized to permit the flow of solvent A into the pump 100.

The value of set point P is subtracted from the value, Q, in summation block 730 to calculate a value, S, which is then compared to the set point, R, for solvent B. If the output of the second decision block 735 is true, the valve 540 will be energized, allowing solvent B to flow into the pump 100.

The value of S is reduced by the value of R in the summation block 740. The result is labeled U in FIG. 7. The value of U is compared with another set point, T, in the third decision block 745. If the output of the third decision block 745 is true, the valve 550 will be energized which allows solvent C to enter the pump 100.

Comparators 725, 735 and 745 provide control to a gradient solenoid logic driver (not shown). Obviously, the circuit can be changed for any number of solenoid values and liquids by changing the decision tree. Note that, at most, only one solvent will be flowing at any instant.

If one of the cylinders does not fill completely on the refill stroke, the pressure controller 215 will accelerate the motor. As long as the pressure controller 215 does not pass $\alpha_7$ 367 and $\alpha_6$ 365 respectively, the control system will compensate for the cylinders not being completely filled.

Figure 6:
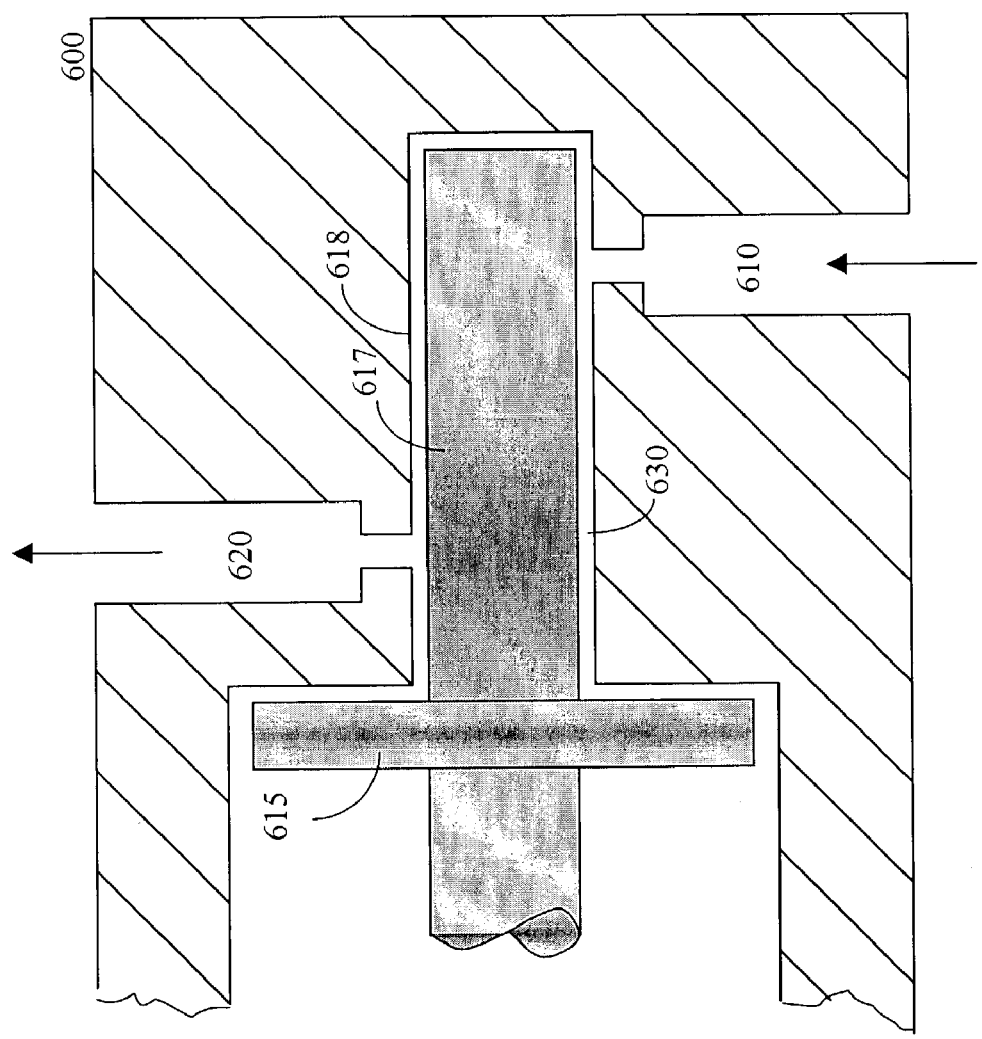
FIG. 6 shows a cutaway of a cylinder head with inlet and outlet ports.

Still another aspect of the present invention is depicted in FIG. 6 with the piston at top dead center. The pump cylinder head 600 (shown in the orientation it will be used) is machined to enhance the mixing of the solvents and solutes. Specifically, the inlet port 610 is located further from the seal 615 than the outlet port 620. Mixing is enhanced within the space between the cylinder wall 618 and the piston 617 the mixing chamber 630. In this fashion, the last solution to enter the mixing chamber 630 is not the first to exit, as is the case when these ports are located directly across from one another.

Obviously many modifications and variations of the present invention are possible in light of the above teachings. It is, therefore, to be understood that within the scope of the appended claims, the invention may be practiced otherwise than as specifically described.

We claim:

1. A method for controlling a reciprocating pump comprising two cylinders with associated pistons, one discharge check valve for each cylinder, and at least one closed interval [$\alpha_1$, $\alpha_2$] where $\alpha$ is an angular displacement; the method comprising:

(a) operating the reciprocating pump at a constant angular speed except through the closed interval [$\alpha_1$, $\alpha_2$]; and (b) varying a angular speed of the reciprocating pump to maintain a constant pump discharge pressure through the closed interval [$\alpha_1$, $\alpha_2$].

2. The method of claim 1 wherein the closed interval $[\alpha_1, \alpha_2]$ is defined such that, in one pump cycle:
   (a) $\alpha_1$ is an angular displacement when a first cylinder's discharge check valve opens; and
   (b) $\alpha_2$ is an angular displacement when a second cylinder's discharge check valve closes.

3. The method of claim 1 wherein, in a single pump cycle, there are two closed intervals, $[\alpha_1, \alpha_2]$ and $[\alpha_3, \alpha_4]$ within which the angular speed of the reciprocating pump is varied to maintain a constant discharge pressure.

4. The method of claim 1 wherein the limits $\alpha_1$ and $\alpha_2$ on the closed interval $[\alpha_1, \alpha_2]$ are determined by the steps:
   (a) measuring the pump discharge pressure;
   (b) measuring the angular displacement, $\alpha$, of the pump;
   (c) calculating a first time derivative of the pump discharge pressure;
   (d) storing a first value of the angular displacement, $\alpha_1$, of the pump when the first time derivative increases sharply; and
   (e) storing a second value of the angular displacement, $\alpha_2$, of the pump when the first time derivative again increases sharply.

5. The method of claim 4 wherein the pump angular speed is held constant during the determination of $\alpha_1$, and $\alpha_2$.

6. The method of claim 1 wherein the discharge check valves are instrumented to indicate their open and closed states and limits $\alpha_1$ and $\alpha_2$ on the closed interval $[\alpha_1, \alpha_2]$ are determined by the steps:
   (a) monitoring signals from the two discharge check valves;
   (b) storing a first value of the angular displacement, $\alpha_1$, of the pump when a first check valve opens; and
   (c) storing a second value of the angular displacement, $\alpha_2$, of the pump when a second check valve closes.

7. The method of claim 1 including a pressure controller to calculate a variable angular speed set point, $\omega_{sp}$, at which angular speed the pump will be operated, and wherein a pressure set point for the pressure controller is a value of pressure measured when the angular displacement, $\alpha$, is not in the closed interval, $[\alpha_1, \alpha_2]$.

8. The method of claim 1 including a pressure controller to calculate a variable angular speed set point, $\omega_{sp}$, at which angular speed the pump will be operated, and wherein a pressure set point for the pressure controller is a value of pressure measured when the angular displacement, $\alpha$, is not in the closed interval, $[\alpha_5, \alpha_6]$.

9. The method of claim 1 including a pressure controller to calculate a variable angular speed set point, $\omega_{sp}$, at which angular speed the pump will be operated, and, wherein a pressure set point for the pressure controller is an average of a plurality of values of pressure, all measured when the angular displacement, $\alpha$, is not in the closed interval, $[\alpha_1, \alpha_2]$.

10. The method of claim 1 including a pressure controller to calculate a variable angular speed set point, $\omega_{sp}$, at which angular speed the pump will be operated, and, wherein a pressure set point for the pressure controller is an average of a plurality of values of pressure, all measured when the angular displacement, $\alpha$, is not in the closed interval, $[\alpha_5, \alpha_6]$.

11. The method of claim 1 wherein a pumping system also includes a valve tree comprising two three-port solenoid valves operating in a cycle to measure three solvents into the pump, said method comprising the steps of:
   (a) configuring said valves such that no more than one path between the three solvents and the pump may be open at a time;
   (b) actuating said valves within the valve tree sequentially with an associated valve actuation logic controller to time actuation of each valve to sequentially meter each of said three solvents into pump through the valve tree; and
   (c) deactivating all valves simultaneously during a time in which both pump inlet check valves are closed.

12. The method of claim 11 wherein each valve is sequentially activated at a time corrected by measuring a delay time between electrical activation and fluid path transfer.

13. The method of claim 1 wherein solvent and solute mixing is enhanced upon induction into the pump by placement of an inlet port and an outlet port in a mixing chamber inside a cylinder head of the pump such that:
   (a) the inlet port is located toward the end farthest from the piston; while
   (b) the outlet port is located closest to the piston.

14. A method for determining a decompression volume in a pump cylinder for low pressure gradient former switching, the method comprising the steps of:
   (a) determining a recompression volume for the pump cylinder;
   (b) determining the decompression volume as a function of the recompression volume; and
   (c) using the decompression volume to time valve openings for low pressure gradient forming.

15. The method of claim 14 wherein the recompression volume is determined by the steps of:
   (a) measuring an angular position of a pump camshaft;
   (b) recording the angular position of the pump camshaft when a discharge check valve opens; and
   (c) correlating the cylinder volume to the angular position of the camshaft.

16. The method of claim 15 wherein the opening of the discharge check valve is detected by the steps of:
   (a) measuring a pressure downstream of the discharge check valve; and
   (c) detecting when the pressure increased sharply.

17. The method of claim 15 wherein the opening of the discharge check valve is detected by a sensor indicating a state of opening of the discharge check valve.

18. The method of claim 14 wherein the function of the recompression volume states that the decompression volume is proportional to the recompression volume.

19. The method of claim 14 wherein a duration of decompression is determined by the steps of:
   (a) measuring an angular position of a pump camshaft;
   (b) sensing a first angular position as the angular position for which a pump piston reaches top dead center;
   (c) utilizing the function of recompression to determine the decompression volume;
   (d) calculating a second angular position as the angular position at which the decompression volume is reached; and
   (e) detecting when the pump camshaft reaches said second angular position at which the decompression volume is reached.

20. The method of claim 14 wherein a relationship between camshaft angular position and cylinder volume is known, a duration of decompression is then determined by the steps of:
   (a) measuring the angular position of a pump camshaft;
   (b) sensing a first angular position as the angular position, $\alpha_0$, for which a pump piston reaches bottom dead center;

(c) sensing a second angular piston, $\alpha_1$, when a discharge check valve opens for the pump piston;
(d) calculating a recompression volume as a function of the first and second angular positions, $\alpha_0$ and $\alpha_1$;
(e) utilizing the function of recompression to determine the decompression volume;
(f) sensing a third angular position as the angular position, $\alpha_6$, for which the pump piston reaches top dead center;
(g) calculating a fourth angular position, $\alpha_7$, as the angular position at which the decompression volume is reached; and
(h) detecting when the pump camshaft reaches said fourth angular position, $\alpha_7$, at which the decompression volume is reached.

21. The method of claim 20 for a two-cylinder pump, the method also comprising the steps of:
(a) sensing a fifth angular position as the angular position, $\alpha_4$, for which a second pump piston reaches bottom dead center;
(b) sensing a sixth angular piston, $\alpha_5$, when a discharge check valve opens for the second pump piston;
(c) calculating a recompression volume as a function of the fifth and sixth angular positions, $\alpha_4$ and $\alpha_5$;
(d) utilizing the function of recompression to determine a second decompression volume;
(e) sensing a seventh angular position as the angular position, $\alpha_2$, for which the second pump piston reaches top dead center;
(f) calculating an eighth angular position, $\alpha_3$, as the angular position at which the second decompression volume is reached; and
(g) detecting when the pump camshaft reaches said eighth angular position, $\alpha_3$, at which the second decompression volume is reached.

22. An apparatus for controlling a reciprocating pump comprising two cylinders with associated pistons, one discharge check valve for each cylinder, and at least one closed interval $[\alpha_1, \alpha_2]$ where $\alpha$ is an angular displacement; the apparatus comprising:
(a) means for operating the reciprocating pump at a constant angular speed except through the closed interval $[\alpha_1, \alpha_2]$; and
(b) means for varying a angular speed of the reciprocating pump to maintain a constant pump discharge pressure through the closed interval $[\alpha_1, \alpha_2]$.

23. The apparatus of claim 22 wherein the closed interval $[\alpha_1, \alpha_2]$ is defined such that, in one pump cycle
(a) $\alpha_1$ is an angular displacement when a first cylinder's discharge check valve opens; and
(b) $\alpha_2$ is an angular displacement when a second cylinder's discharge check valve closes.

24. The apparatus of claim 22 wherein, in a single pump cycle, there are two closed intervals, $[\alpha_1, \alpha_2]$ and $[\alpha_3, \alpha_4]$ within which the means for varying the angular speed of the reciprocating pump includes means for maintaining a constant discharge pressure.

25. The apparatus of claim 22 wherein the limits $\alpha_1$ and $\alpha_2$ on the closed interval $[\alpha_1, \alpha_2]$ are determined using:
(a) a pressure sensor for measuring the pump discharge pressure;
(b) an angular displacement sensor for measuring the angular displacement, $\alpha$, of the pump;
(c) means for calculating a first temporal derivative of the pump discharge pressure;
(d) memory for storing a first value of the angular displacement, $\alpha_1$, of the pump when the first time derivative increases sharply; and
(e) memory for storing a second value of the angular displacement, $\alpha_2$, of the pump when the first time derivative again increases sharply.

26. The apparatus of claim 25 including means for holding the pump angular speed constant during the determination of $\alpha_1$ and $\alpha_2$.

27. The apparatus of claim 22 wherein the discharge check valves are supplied with sensors to indicate their open and closed states and limits $\alpha_1$ and $\alpha_2$ on the closed interval $[\alpha_1, \alpha_2]$ are determined using:
(a) means for monitoring signals from the two discharge check valves;
(b) means for storing a first value of the angular displacement, $\alpha_1$, of the pump when a first check valve opens; and
(c) means for storing a second value of the angular displacement, $\alpha_2$, of the pump when a second check valve closes.

28. The apparatus of claim 22 including a pressure controller means to calculate a variable angular speed set point, $\omega_{sp}$, at which angular speed the pump will be operated, and a pressure sensor to measure a pressure set point for the pressure controller when the angular displacement, $\alpha$, is not in the closed interval, $[\alpha_1, \alpha_2]$.

29. The apparatus of claim 28 including a pressure controller means to calculate a variable angular speed set point, $\omega_{sp}$, at which angular speed the pump will be operated, and a pressure sensor to measure a pressure set point for the pressure controller when the angular displacement, $\alpha$, is not in a second closed interval, $[\alpha_5, \alpha_6]$ associated with a second cylinder in the pump.

30. The apparatus of claim 22 including a pressure controller to calculate a variable angular speed set point, $\omega_{sp}$, at which angular speed the pump will be operated, and including means for calculating a pressure set point for the pressure controller as an average of a plurality of values of pressure, all measured when the angular displacement, $\alpha$, is not in the closed interval, $[\alpha_1, \alpha_2]$.

31. The apparatus of claim 30 including a pressure controller to calculate a variable angular speed set point, $\omega_{sp}$, at which angular speed the pump will be operated, and including means for calculating a pressure set point for the pressure controller as an average of a plurality of values of pressure, all measured when the angular displacement, $\alpha$, is not in a second closed interval, $[\alpha_5, \alpha_6]$ associated with a second cylinder in the pump.

32. The apparatus of claim 22 wherein a pumping system also includes a valve tree comprising two three-port valves to meter three solvents into the pump, said apparatus comprising:
(a) configuring said valves such that at most one path between the three solvents and the pump may be open at a time;
(b) actuators for actuating said valves within the valve tree sequentially with an associated valve actuation logic controller means to time actuation of each valve to sequentially meter each of said three solvents into pump through the valve tree; and
(c) means for deactivating all valves simultaneously during a time in which both pump inlet check valves are closed.

33. The apparatus of claim 32 including a clock measuring a delay time between electrical activation and fluid path transfer wherein each valve is sequentially activated at a time corrected by said a delay time.

34. The apparatus of claim 22 wherein solvent and solute mixing is enhanced upon induction into the pump by placement of an inlet port and an outlet port in a mixing chamber inside a cylinder head of the pump such that:
(a) the inlet port is located toward the end farthest from the piston; while
(b) the outlet port is located closest to the piston.

35. An apparatus for determining a decompression volume in a pump cylinder for low pressure gradient former switching, the apparatus comprising:
(a) means for determining a recompression volume for the pump cylinder;
(b) means for determining the decompression volume as a function of the recompression volume; and
(c) means for using the decompression volume to time valve openings for low pressure gradient forming.

36. The apparatus of claim 35 wherein the means for determining the recompression volume includes additional components comprising:
(a) an angular position sensor for a pump camshaft;
(b) a recorder for recording the angular position of the pump camshaft when a discharge check valve opens; and
(c) means for correlating the cylinder volume to the angular position of the camshaft.

37. The apparatus of claim 36 wherein the opening of the discharge check valve is detected using components comprising:
(a) a pressure sensor for measuring a pressure downstream of the discharge check valve; and
(c) a pressure-change detecting means for detecting when the pressure increases sharply.

38. The apparatus of claim 36 including a sensor indicating a state of opening of the discharge check valve for detecting the opening of the discharge check valve.

39. The apparatus of claim 35 including means for calculating the function of the recompression volume by multiplying the decompression volume by a constant factor.

40. The apparatus of claim 35 wherein a duration of decompression is determined, the apparatus comprising:
(a) an angular position sensor for measuring an angular position of a pump camshaft;
(b) means for sensing a first angular position as the angular position for which a pump piston reaches top dead center;
(c) means for utilizing the function of recompression to determine the decompression volume;
(d) means for calculating a second angular position as the angular position at which the decompression volume is reached; and
(e) means for detecting when the pump camshaft reaches said second angular position at which the decompression volume is reached.

41. The apparatus of claim 35 wherein a relationship between camshaft angular position and cylinder volume is known, a duration of decompression is then determined by the apparatus comprising:
(a) an angular position sensor for measuring the angular position of a pump camshaft;
(b) means for sensing a first angular position as the angular position, $\alpha_0$, for which a pump piston reaches bottom dead center;
(c) means for sensing a second angular piston, $\alpha_1$, when a discharge check valve opens for the pump piston;
(d) means for calculating a recompression volume as a function of the first and second angular positions, $\alpha_0$ and $\alpha_1$;
(e) means for utilizing the function of recompression to determine the decompression volume;
(f) means for sensing a third angular position as the angular position, $\alpha_6$, for which the pump piston reaches top dead center;
(g) means for calculating a fourth angular position, $\alpha_7$, as the angular position at which the decompression volume is reached; and
(h) means for detecting when the pump camshaft reaches said fourth angular position, $\alpha_7$, at which the decompression volume is reached.

42. The apparatus of claim 41 for a two-cylinder pump, the apparatus also comprising:
(a) means for sensing a fifth angular position as the angular position, $\alpha_4$, for which a second pump piston reaches bottom dead center;
(b) means for sensing a sixth angular piston, $\alpha_5$, when a discharge check valve opens for the second pump piston;
(c) means for calculating a recompression volume as a function of the fifth and sixth angular positions, $\alpha_4$, and $\alpha_5$;
(d) means for utilizing the function of recompression to determine a second decompression volume;
(e) means for sensing a seventh angular position as the angular position, $\alpha_2$, for which the second pump piston reaches top dead center;
(f) means for calculating an eighth angular position, $\alpha_3$, as the angular position at which the second decompression volume is reached; and
(g) means for detecting when the pump camshaft reaches said eighth angular position, $\alpha_3$, at which the second decompression volume is reached.

* * * * *